(12) United States Patent
Pataut et al.

(10) Patent No.: US 7,655,219 B2
(45) Date of Patent: Feb. 2, 2010

(54) COSMETIC HAIR TREATMENT COMPOSITION COMPRISING A NONASSOCIATIVE FIXING POLYURETHANE AND AN ANIONIC OR NONIONIC ASSOCIATIVE POLYURETHANE, AND COSMETIC TREATMENT PROCESS

(75) Inventors: Françoise Pataut, Paris (FR); Charles Gringore, Paris (FR)

(73) Assignee: L'Oreal, Paris (FR)

( * ) Notice: Subject to any disclaimer, the term of this patent is extended or adjusted under 35 U.S.C. 154(b) by 240 days.

(21) Appl. No.: 10/279,036

(22) Filed: Oct. 24, 2002

(65) Prior Publication Data
US 2003/0103909 A1 Jun. 5, 2003

(30) Foreign Application Priority Data
Oct. 26, 2001 (FR) .................................. 01 13904

(51) Int. Cl.
*A61Q 5/06* (2006.01)
(52) U.S. Cl. .................. 424/70.11; 424/70.12; 132/203
(58) Field of Classification Search ........................ None
See application file for complete search history.

(56) References Cited

U.S. PATENT DOCUMENTS

| | | | |
|---|---|---|---|
| 5,626,840 A * | 5/1997 | Thomaides et al. ...... | 424/70.11 |
| 5,968,494 A | 10/1999 | Kukkala et al. | |
| 6,080,392 A | 6/2000 | Dupuis et al. ............ | 424/70.16 |
| 6,166,093 A | 12/2000 | Mougin et al. | |
| 6,372,876 B1 | 4/2002 | Kim et al. | |
| 6,410,004 B1 | 6/2002 | Kim et al. | |
| 6,585,965 B1 * | 7/2003 | Carballada et al. ......... | 424/70.1 |
| 6,613,315 B1 | 9/2003 | Dupuis .................... | 424/70.17 |
| 6,630,133 B1 * | 10/2003 | Dupuis ...................... | 424/70.1 |

FOREIGN PATENT DOCUMENTS

| | | |
|---|---|---|
| EP | 1 062 935 | 12/2000 |
| EP | 1 132 076 | 9/2001 |
| FR | 2 774 899 | 8/1999 |
| WO | WO 00/12055 | 3/2000 |
| WO | WO 01/54660 | 8/2001 |

* cited by examiner

*Primary Examiner*—Jyothsna A Venkat
(74) *Attorney, Agent, or Firm*—Steptoe & Johnson LLP

(57) ABSTRACT

The present invention relates to a cosmetic hair treatment composition comprising, in a cosmetically acceptable medium, at least one nonassociative fixing polyurethane and at least one anionic or nonionic associative polyurethane, packaged in an aerosol device in the presence of a propellant. The invention also relates to a cosmetic treatment process using said cosmetic treatment composition, and also to a use as a leave-in styling product.

8 Claims, No Drawings

COSMETIC HAIR TREATMENT COMPOSITION COMPRISING A NONASSOCIATIVE FIXING POLYURETHANE AND AN ANIONIC OR NONIONIC ASSOCIATIVE POLYURETHANE, AND COSMETIC TREATMENT PROCESS

The present invention relates to a cosmetic hair treatment composition containing, in combination, at least one nonassociative fixing polyurethane and at least one anionic or nonionic associative polyurethane, packaged in an aerosol device, and also to a cosmetic treatment process using this composition.

Styling products, such as lacquers, mousses and gels, are well known in the art and are usually used to structure the hairstyle and to give it long-lasting hold.

Styling products generally contain anionic or nonionic fixing polymers in a cosmetically acceptable medium.

However, certain polymers cause the hair to harden. The hair is then often stuck together and the hairstyle is fixed.

Applicant have found, surprisingly, that by combining a nonassociative fixing polyurethane and an anionic or nonionic associative polyurethane in an aerosol medium, shaping of the hairstyle is obtained by simple working with the fingers, and that this combination overcomes the drawbacks as described above that are encountered with the usual fixing products.

This composition also has the advantage of spreading well on the hair, and can be applied either to dry hair or to wet hair.

In the case of an application to wet hair, the hair may be dried in the open air or with a hair dryer. This results in a supple and natural hairstyle.

One subject of the invention is thus a cosmetic hair treatment composition as described below.

Another subject of the present invention is a cosmetic hair treatment process using the composition according to the invention.

A subject of the invention is also the use of the composition according to the invention as a styling product.

Other subjects, characteristics, aspects and advantages of the invention will emerge even more clearly on reading the description and the various examples that follow.

The present invention relates to a cosmetic hair treatment composition comprising, in a cosmetically acceptable medium, at least one nonassociative fixing polyurethane and at least one anionic or nonionic associative polyurethane, packaged in an aerosol device in the presence of a propellant.

The expression "cosmetically acceptable medium" means a medium that is compatible with the hair, but that also has a pleasant odor, appearance and feel.

For the purposes of the present invention, the expression "nonassociative fixing polyurethane" means polycondensates comprising at least one polyurethane block capable of providing hold to the hairstyle, which do not comprise in their structure a terminal or pendent fatty chain containing more than ten carbon atoms. They are described in particular in patents EP 0 751 162, EP 0 637 600, FR 2 743 297 and EP 0 648 485 which are commonly assigned to the same assignee the present application, and also patents EP 0 656 021 or WO 94/03510 to BASF and EP 0 619 111 to National Starch.

The nonassociative fixing polyurethanes used in accordance with the invention may be soluble in the cosmetically acceptable medium, especially after neutralization with an organic or mineral base, or alternatively they may form a dispersion in this medium.

In this case, the dispersion may comprise at least 0.05% of surfactant enabling the dispersion and maintenance in dispersion of the nonassociative fixing polyurethane.

According to the invention, any type of surfactant can be used in said dispersion, but preferably a nonionic surfactant. The average size of the nonassociative fixing polyurethane particles in the dispersion is preferably between 0.1 and 1 micron.

By way of example, the nonassociative fixing polyurethane can be formed by an arrangement of blocks, this arrangement being obtained in particular from:
  (1) at least one compound which contains two or more than two active hydrogen atoms per molecule;
  (2) at least one diol or a mixture of diols containing acid functions or their salts; and
  (3) at least one di- or polyisocyanate.

Advantageously, the compounds (1) are chosen from the group comprising diols, diamines, polyesterols and polyetherols, or mixtures thereof.

The compounds (1) that are preferred are linear polyethylene glycols and polypropylene glycols, in particular those that are obtained by reaction of ethylene oxide or propylene oxide with water or diethylene or dipropylene glycol in the presence of sodium hydroxide as catalyst. These polyalkylene glycols generally have a molecular mass of between about 600 and 20,000.

Other preferred organic compounds are those that have mercapto, amino, carboxyl or hydroxyl groups. Among these, mention may be made more particularly of polyhydroxylated compounds such as polyether diols, polyester diols, polyacetal diols, polyamide diols, polyesterpolyamide diols, poly(alkylene ether) diols, polythioether diols and polycarbonate diols.

The preferred polyether diols are, for example, the condensation products of ethylene oxide, of propylene oxide or of tetrahydrofuran, their copolymerization or condensation products, which may be grafted or blocks, such as mixtures of condensates of ethylene oxide and propylene oxide, and the products of polymerization of olefins, at high pressure, with alkylene oxide condensates. Suitable polyethers are prepared, for example, by condensation of alkylene oxides and polyhydric alcohols, such as ethylene glycol, 1,2-propylene glycol and 1,4-butanediol.

The polyester diols, polyesteramides and polyamide diols are preferably saturated and are obtained, for example, from the reaction of saturated or unsaturated polycarboxylic acids with polyhydric alcohols, diamines or polyamines. Adipic acid, succinic acid, phthalic acid, terephthalic acid and maleic acid can be used, for example, to prepare these compounds. Polyhydric alcohols that are suitable for preparing the polyesters include, for example, ethylene glycol, 1,2-propylene glycol, 1,4-butanediol, neopentyl glycol and hexanediol. Amino alcohols, for example ethanolamine, can also be used. Diamines that are suitable for preparing the polyesteramides are ethylenediamine and hexamethylenediamine.

Suitable polyacetals can be prepared, for example, from 1,4-butanediol or from hexanediol and from formaldehyde. Suitable polythioethers can be prepared, for example, by condensation reaction between thioglycols, either alone or in combination with other glycols such as ethylene glycol, 1,2-propylene glycol or with other polyhydroxylated compounds. Polyhydroxylated compounds already containing urethane groups, natural polyols, which can be further modified, for example castor oil and carbohydrates, can also be used.

More preferably, the compound of group (1) is a polyesterol, in particular a polyester diol formed by the reaction of at least one (di)polyol ($1_a$) and at least one acid ($1_b$). The (di)polyol ($1_a$) is chosen in particular from the group comprising neopentyl glycol, 1,4-butanediol, hexanediol, ethylene glycol, diethylene glycol, propylene glycol, butylene glycol, neopentyl glycol and (di)polyethylene glycol. The acid ($1_b$) is chosen in particular from the group comprising phthalic acid, isophthalic acid, adipic acid and (poly)lactic acid.

A hydroxycarboxylic acid such as dimethylol-propanoic acid (DMPA) or a 2,2-hydroxymethylcarboxylic acid can be used in particular as compound (2). In general, the compound (2) is useful as a coupling block. The preferred compounds (2) are those comprising at least one poly((α-hydroxydiolcarboxylic) acid).

The compounds (2) that are particularly preferred in accordance with the invention are those chosen from the group comprising 2,2-di(hydroxy-methyl)acetic acid, 2,2-dihydroxymethylpropionic acid, 2,2-dihydroxymethylbutyric acid and 2,2-dihydroxy-methylpentanoic acid.

The di- or polyisocyanate (3) can be chosen in particular from the group comprising hexamethylene diisocyanate, isophorone diisocyanate (IPDI), tolylene diisocyanate, 4,4'-diphenylmethane diisocyanate (DPMD) and 4,4'-dicyclohexylmethane diisocyanate (DCMD), methylenebis(p-phenyl) diisocyanate, methylenebis(4-cyclohexyl isocyanate), toluene diisocyanates, 1,5-naphthalene diisocyanate, 4,4'-diphenylmethane diisocyanate, 2,2'-dimethyl-4,4'-diphenylmethane diisocyanate, 1,3-phenylene diisocyanate, 1,4-phenylene diisocyanate, mixtures of 2,4- and 2,6-toluene diisocyanate, 2,2'-dichloro-4,4'-diisocyanatodiphenylmethane, 2,4-dibromo-1,5-diisocyanatonaphthalene, 1,4-butane diisocyanate, 1,6-hexane diisocyanate and 1,4-cyclohexane diisocyanate.

The nonassociative fixing polyurethane can be formed using an additional compound (4) that generally serves to extend its chain. These compounds (4) can be chosen from the group comprising, in particular, saturated or unsaturated glycols such as ethylene glycol, diethylene glycol, neopentyl glycol or triethylene glycol; amino alcohols such as ethanolamine, propanolamine or butanolamine; heterocyclic, aromatic, cycloaliphatic and aliphatic primary amines; diamines; carboxylic acids such as aliphatic, aromatic or heterocyclic carboxylic acids, for instance oxalic acid, succinic acid, glutaric acid, adipic acid, sebacic acid or terephthalic acid; and amino carboxylic acids. The preferred compounds (4) are aliphatic diols.

The nonassociative fixing polyurethanes used according to the invention can also be formed from additional compounds (5) having a silicone skeleton, such as polysiloxanes, polyalkylsiloxanes or polyarylsiloxanes, in particular polyethylsiloxanes, polymethylsiloxanes and polyphenylsiloxanes, optionally containing hydrocarbon-based chains grafted onto the silicon atoms.

The nonassociative fixing polyurethanes used advantageously comprise a repeating base unit corresponding to the general formula (I):

$$\text{—O—B—O—CO—NH—R—NH—CO—} \quad \text{(I)}$$

in which:

B is a divalent $C_1$ to $C_{30}$ hydrocarbon-based group, this group possibly being substituted with a group comprising one or more carboxylic acid functions and/or one or more sulfonic acid functions, said carboxylic acid and/or sulfonic acid functions being in free form or partially or totally neutralized with a mineral or organic base, and R is a divalent group chosen from alkylene groups of aromatic type, $C_1$ to $C_{20}$ aliphatic groups and $C_1$ to $C_{20}$ cycloaliphatic groups, these groups possibly being substituted.

The group R is advantageously chosen from the groups corresponding to the following formulae:

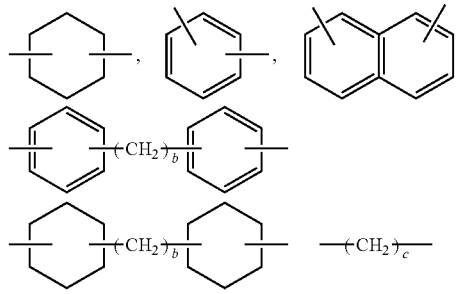

in which b is an integer between 0 and 3 and c is an integer between 1 and 20, preferably between 2 and 12.

In particular, the group R is chosen from hexamethylene, 4,4'-biphenylenemethane, 2,4- and/or 2,6-tolylene, 1,5-naphthylene, p-phenylene and methylene-4,4-bis(cyclohexyl) groups and the divalent group derived from isophorone.

The nonassociative fixing polyurethane used in the present invention can advantageously also comprise at least one polysiloxane block whose repeating base unit corresponds, for example, to the general formula (II) below:

$$\text{—O—P—O—CO—NH—R—NH—CO—} \quad \text{(II)}$$

in which:

P is a polysiloxane segment, and

R is a divalent group chosen from alkylene groups of aromatic type, $C_1$ to $C_{20}$ aliphatic groups and $C_1$ to $C_{20}$ cycloaliphatic groups, these groups possibly being substituted.

Advantageously, the polysiloxane segment P corresponds to the general formula (III) below:

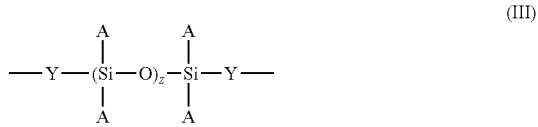

in which:

the groups A, which may be identical or different, are chosen, on the one hand, from $C_1$ to $C_{20}$ monovalent hydrocarbon-based groups which are free or substantially free of ethylenic unsaturation and, on the other hand, from aromatic groups, Y represents a divalent hydrocarbon-based group, and z represents an integer chosen such that the average molecular mass of the polysiloxane segment is between 300 and 10,000.

In general, the divalent group Y is chosen from alkylene groups of formula $-(CH_2)_a-$, in which a represents an integer which can be between 1 and 10.

The groups A can be chosen from alkyl groups, in particular methyl, ethyl, propyl, isopropyl, butyl, pentyl, hexyl, octyl, decyl, dodecyl and octadecyl groups; cycloalkyl groups, in particular the cyclohexyl group; aryl groups, in particular phenyl and naphthyl; arylalkyl groups, in particular benzyl and phenylethyl, and also tolyl and xylyl groups.

Examples of nonassociative fixing polyurethanes that may especially be mentioned include the dimethylolpropionic acid/isophorone diisocyanate/neopentyl glycol/polyester diols copolymer (also known as polyurethane-1, INCI name) sold under the brand name Luviset® PUR by the company BASF, and the dimethylolpropionic acid/isophorone diisocyanate/neopentyl glycol/polyester diols/diamino silicone copolymer (also known as polyurethane-6, INCI name) sold under the brand name Luviset® Si PUR A by BASF.

The nonassociative fixing polyurethanes are especially used in an amount from 0.1% to 20% by weight, preferably from 0.5% to 10% by weight and better still from 1% to 5% by weight, relative to the total weight of the hair treatment composition.

The expression "associative polyurethane" means a polyurethane containing at least one terminal or pendent fatty chain containing at least 10 carbon atoms. This type of polymer is capable of interacting with itself or with particular compounds such as surfactants to result in thickening of the medium.

An example of an anionic associative polyurethane that may especially be mentioned is an acrylic terpolymer that is soluble or swellable in alkalis. It is characterized in that it comprises:

a) about 20% to 70% by weight, preferably 25% to 55% by weight, of a carboxylic acid containing α,β-monoethylenic unsaturation;

b) about 20% to 80% by weight, preferably 30% to 65% by weight, of a nonsurfactant monomer containing monoethylenic unsaturation, which is different than a), and c) about 0.5% to 60% by weight, preferably 10% to 50% by weight, of a nonionic urethane monomer which is the product of reaction of a monohydric nonionic surfactant with a monoisocyanate containing monoethylenic unsaturation.

The carboxylic acid containing α,β-monoethylenic unsaturation a) can be chosen from many acids and in particular acrylic acid, methacrylic acid, itaconic acid and maleic acid. Methacrylic acid is preferred. A large proportion of acid is essential in order to give a polymer structure that dissolves and gives a thickening effect by reaction with an alkaline compound such as sodium hydroxide, alkanolamines, aminomethylpropanol or aminomethylpropanediol.

The terpolymer should also contain a large proportion, indicated above, of a monomer b) containing monoethylenic unsaturation that has no surfactant properties. The preferred monomers are those which give polymers that are water-insoluble when they are homopolymerized, and are illustrated by $C_1$-$C_4$ alkyl acrylates and methacrylates such as methyl acrylate, ethyl acrylate and butyl acrylate, or the corresponding methacrylates. The monomers more particularly preferred are the methyl and ethyl (meth)acrylates. Other monomers that can be used are styrene, vinyltoluene, vinyl acetate, acrylonitrile and vinylidene chloride. Nonreactive monomers are preferred, such monomers being those in which the single ethylenic group is the only group that is reactive under the polymerization conditions. However, monomers which contain groups that are reactive under the action of heat can be used in certain situations, for instance hydroxyethyl acrylate.

The monohydric nonionic surfactants used to obtain the nonionic urethane monomer c) are well known and are generally alkoxylated hydrophobic compounds containing an alkylene oxide forming the hydrophilic part of the molecule. The hydrophobic compounds generally consist of an aliphatic alcohol or an alkylphenol in which a carbon chain containing at least six carbon atoms constitutes the hydrophobic part of the surfactant.

The preferred monohydric nonionic surfactants have the formula:

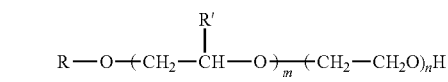

in which R is a $C_6$-$C_{30}$ alkyl or $C_8$-$C_{30}$ aralkyl group, R' is a $C_1$-$C_4$ alkyl group, n is an average number ranging approximately from 5 to 150 and m is an average number ranging approximately from 0 to 50, with the condition that n is at least as large as m and that n+m=5–150.

Preferred $C_6$-$C_{30}$ alkyl groups that may be mentioned include dodecyl and $C_{18}$-$C_{26}$ alkyl radicals. Aralkyl groups that may be mentioned more particularly include ($C_8$-$C_{13}$) alkylphenyl groups. The preferred group R' is the methyl group.

The monoisocyanate containing monoethylenic unsaturation that is used to form the nonionic urethane monomer c) can be chosen from a wide variety of compounds. A compound containing any copolymerizable unsaturation such as acrylic or methacrylic unsaturation can be used. An allylic unsaturation imparted by allyl alcohol can also be used. The preferred monoethylenic monoisocyanates are α,α-dimethyl-m-isopropenylbenzyl isocyanate and methylstyreneisopropyl isocyanate.

The acrylic terpolymer defined above is obtained by aqueous emulsion copolymerization of the components a), b) and c) which is entirely common and described in patent application EP-A-0 173 109.

As examples of anionic associative polyurethanes that may be used according to the present invention, mention may be made especially of copolymers of methacrylic or acrylic acid comprising at least one $C_1$-$C_{30}$ alkyl (meth)acrylate unit and a urethane unit substituted with a fatty chain. Mention may be made in particular of the methacrylic acid/methyl methacrylate/methylstyreneisopropyl isocyanate/polyethoxylated behenyl alcohol copolymer (comprising 40 ethoxy units) sold under the brand name Viscophobe® DB 1000 sold by Union Carbide.

The nonionic associative polyurethanes used in the present invention are especially polyurethane polyethers comprising in their chain both hydrophilic blocks usually of polyoxyethylenated nature, and hydrophobic blocks that may be aliphatic sequences alone and/or cycloaliphatic and/or aromatic sequences.

Preferably, the polyurethane polyethers comprise at least two hydrocarbon-based lipophilic chains, containing from 6 to 30 carbon atoms, separated by a hydrophilic block, the hydrocarbon-based chains possibly being pendent chains or chains at the end of a hydrophilic block. In particular, it is possible for one or more pendent chains to be provided. In addition, the polymer may comprise a hydrocarbon-based chain at one or both ends of a hydrophilic block.

The polyurethane polyethers may be multiblock, in particular in triblock form. The hydrophobic blocks may be at each end of the chain (for example: triblock copolymer containing a hydrophilic central block) or distributed both at the ends and within the chain (for example multiblock copolymer). These same polymers may also be graft polymers or starburst polymers.

The fatty-chain nonionic polyurethane polyethers may be triblock copolymers whose hydrophilic block is a polyoxyethylenated chain comprising from 50 to 1000 ethoxylated groups. The nonionic polyurethane polyethers comprise a urethane bond between the hydrophilic blocks, whence arises the name.

By extension, also featured among the fatty-chain nonionic polyurethane polyethers are those whose hydrophilic blocks are linked to the lipophilic blocks via other chemical bonds.

As examples of fatty-chain nonionic polyurethane polyethers that may be used in the invention, mention may also be made of Rheolate® 205 containing a urea function, sold by Rheox, or alternatively Rheolate® 208, 204 or 212, and also Acrysol® RM 184.

Mention may also be made of the product Elfacos® T210 containing a $C_{12-14}$ alkyl chain and the product Elfacos® T212 containing a $C_{18}$ alkyl chain, from Akzo.

The product DW 1206B from Rohm & Haas, containing a $C_{20}$ alkyl chain and a urethane bond, sold at a solids content of 20% in water, may also be used.

Solutions or dispersions of these polymers, especially in water or in aqueous-alcoholic medium, may also be used. Examples of such polymers that may be mentioned include Rheolate® 255, Rheolate® 278 and Rheolate® 244 sold by Rheox. The products DW 1206F and DW 1206J sold by Rohm & Haas may also be used.

The polyurethane polyethers that may be used according to the invention are in particular those described in the article by G. Formum, J. Bakke and Fk. Hansen—*Colloid Polym. Sci.* 271, 380-389 (1993).

As preferred examples of nonionic associative polyurethanes, mention may be made of the polyether-polyurethanes that may be obtained by polycondensation of at least three compounds comprising (i) at least one polyethylene glycol comprising from 150 to 180 mol of ethylene oxide, (ii) stearyl alcohol or decyl alcohol, and (iii) at least one diisocyanate.

Such polyether-polyurethanes are sold especially by the company Rohm & Haas under the names Aculyn® 46 and Aculyn® 44. Aculyn® 46 is a polycondensate of polyethylene glycol containing 150 or 180 mol of ethylene oxide, of stearyl alcohol and of methylenebis(4-cyclohexyl isocyanate) (SMDI), at a concentration of 15% by weight in a matrix of maltodextrin (4%) and water (81%); Aculyn® 44 is a polycondensate of polyethylene glycol containing 150 or 180 mol of ethylene oxide, of decyl alcohol and of methylenebis (4-cyclohexyl isocyanate) (SMDI), at a concentration of 35% by weight in a mixture of propylene glycol (39%) and water (26%).

The anionic or nonionic associative polyurethanes are especially used in an amount from 0.1% to 10% by weight, preferably from 0.2% to 8% by weight and better still from 0.5% to 5% by weight, relative to the total weight of the hair treatment composition.

Any propellant that is well known in the art may be used in the present invention, such as hydrocarbon-based gases, for instance $C_3$-$C_5$ alkanes, for example propane, n-butane or isobutane; fluorinated gases such as, for example, chlorodifluoromethane, dichlorodifluoromethane, 1,1-difluoroethane, chlorodifluoroethane or dichlorotetrafluoroethane; nitrogen, air and carbon dioxide; dimethyl ether; and mixtures thereof.

Dimethyl ether, hydrocarbon-based gases or mixtures thereof, such as, for example, mixtures of dimethyl ether and of $C_{3-5}$ alkanes, are preferably used.

The propellants are especially used in an amount from 2% to 90% by weight and preferably from 5% to 80% by weight, relative to the total weight of the hair treatment composition.

The cosmetically acceptable medium may consist solely of water or of a mixture of water and a cosmetically acceptable solvent such as a $C_1$-$C_4$ lower alcohol, such as ethanol, isopropanol, tert-butanol or n-butanol; alkylene polyols, for instance propylene glycol; polyol ethers; and mixtures thereof.

The composition according to the invention may also comprise standard additives that are well known in the art, such as other fixing polymers different than those described above, cationic, amphoteric or zwitterionic polymers, other anionic or nonionic polymers different than those described above, thickeners, nacreous agents, opacifiers, UV screening agents, sugars, fragrances, mineral, plant and/or synthetic oils, fatty acid esters, colorants, volatile or nonvolatile, cyclic or acyclic, branched or unbranched silicones, which may or may not be organomodified, natural or synthetic, mineral or organic particles, preserving agents and pH stabilizers.

A person skilled in the art will take care to select the optional additives and the amount thereof such that they do not harm the properties of the compositions of the present invention.

These additives are present in the composition according to the invention in an amount ranging from 0 to 20% by weight relative to the total weight of the composition.

The hair treatment compositions in accordance with the invention may be in the form of a mousse, a gel, a spray or a lacquer, and may be used in rinse-out or leave-in application. They are packaged in an aerosol device that is common in cosmetics.

The compositions in accordance with the invention may be used as hairstyle fixing and/or hold products, haircare compositions, shampoos, hair conditioning compositions, such as compositions for giving the hair softness, or alternatively hair makeup compositions.

The present invention also relates to a cosmetic hair treatment process which consists in applying on the hair an effective amount of the composition as described above, and in optionally rinsing it out, after an optional period in which it is left on the hair.

According to one preferred embodiment of the invention, the composition may be used as a leave-in styling product.

The example that follows illustrates the present invention and should not in any way be considered as limiting the invention.

EXAMPLES

A styling product is prepared in the form of an aerosol spray, comprising not more than 55% of volatile organic compounds, using the following ingredients. The amounts are indicated as percentages by weight:

| | |
|---|---|
| Luviset ® Si PUR sold by BASF | 6.5% |
| Viscophobe ® DB 1000 sold by Union Carbide | 1% |
| Aminomethylpropanol | 0.1% |
| Ethanol | 17% |
| Dimethyl ether | 35% |
| Water qs | 100% |

This styling product is sprayed onto the hair and the hairstyle is shaped. Good hairstyle hold is obtained.

The invention claimed is:

1. A cosmetic hair treatment composition packaged in an aerosol device comprising, in a cosmetically acceptable medium, nonassociative fixing polyurethane wherein the nonassociative fixing polyurethane is present in an amount from 1% to 5% by weight wherein the nonassociative fixing polyurethane is a dimethylolpropionic acid/isophorone diisocyanate/neopentyl glycol/polyester diol copolymer; and anionic associative polyurethane wherein the anionic associative polyurethane is a methacrylic acid/methyl methacrylate/methylstyreneisopropyl isocyanate/polyethoxylated behenyl alcohol copolymer comprising 40 ethoxy units wherein the anionic associative polyurethane is present in an amount from 0.5% to 5% by weight; wherein the cosmetically acceptable medium consists of a mixture of water and a cosmetically acceptable solvent; wherein the cosmetically acceptable solvent is ethanol, isopropanol, tert-butanol, n-butanol or propylene glycol wherein the composition is in the form of a spray and, packaged in the aerosol device in the presence of a propellant.

2. The cosmetic hair treatment composition according to claim 1, wherein the propellant is a hydrocarbon-based gas, a fluorinated gas, nitrogen, air, carbon dioxide, dimethyl ether or mixtures thereof.

3. The cosmetic hair treatment composition according to claim 2, wherein the propellant is dimethyl ether, a hydrocarbon-based gas, or mixtures thereof.

4. The cosmetic hair treatment composition according to claim 1, wherein the propellant is present in an amount from 2% to 90% by weight relative to the total weight of the composition.

5. The cosmetic hair treatment composition according to claim 4, wherein the propellant is present in an amount from 5% and 80% by weight.

6. The cosmetic hair treatment composition according to claim 1, wherein the composition further comprises an additive which is another fixing polymer, a cationic, amphoteric or zwitterionic polymer, another anionic or nonionic polymer, a thickener, a nacreous agent, an opacifier, a UV screening agent, a sugar, a fragrance, a mineral, plant and/or synthetic oil, a fatty acid ester, a colorant, a volatile or nonvolatile, cyclic or acyclic, branched or unbranched silicone, nonorganomodified or organomodified, a natural or synthetic, mineral or organic particle, a preserving agent or a pH stabilizer.

7. A method of styling hair, comprising the step of applying the cosmetic hair treatment composition according to claim 1 to the hair.

8. The cosmetic hair treatment composition according to claim 1 wherein the composition is a leave-in styling product.

* * * * *